United States Patent
Neiers et al.

(10) Patent No.: US 10,106,801 B2
(45) Date of Patent: Oct. 23, 2018

(54) AUTO-INDUCIBLE EXPRESSION SYSTEM

(71) Applicants: UNIVERSITE DE BOURGOGNE, Dijon (FR); INRA, Paris (FR); INSERM, Paris (FR)

(72) Inventors: Fabrice Neiers, Pluvault (FR); Renaud Seigneuric, Magny sur Tille (FR); Loïc Briand, Saint Apollinaire (FR); Carmen Garrido-Fleury, Talant (FR)

(73) Assignees: UNIVERSITE DE BOURGOGNE, Dijon (FR); INRA, Paris (FR); INSERM, Paris (FR)

( * ) Notice: Subject to any disclaimer, the term of this patent is extended or adjusted under 35 U.S.C. 154(b) by 0 days.

(21) Appl. No.: 15/514,028

(22) PCT Filed: Sep. 21, 2015

(86) PCT No.: PCT/EP2015/071619
§ 371 (c)(1),
(2) Date: Mar. 24, 2017

(87) PCT Pub. No.: WO2016/046137
PCT Pub. Date: Mar. 31, 2016

(65) Prior Publication Data
US 2017/0298367 A1    Oct. 19, 2017

(30) Foreign Application Priority Data
Sep. 24, 2014 (FR) ..................... 14 59019

(51) Int. Cl.
| C12P 21/02 | (2006.01) |
| C12N 15/72 | (2006.01) |
| C12N 15/74 | (2006.01) |
| C07K 14/47 | (2006.01) |
| C12N 9/12 | (2006.01) |
| C12P 21/00 | (2006.01) |
| C12N 1/20 | (2006.01) |

(52) U.S. Cl.
CPC .............. *C12N 15/72* (2013.01); *C07K 14/47* (2013.01); *C12N 1/20* (2013.01); *C12N 9/1247* (2013.01); *C12N 15/74* (2013.01); *C12P 21/00* (2013.01); *C12Y 207/07006* (2013.01)

(58) Field of Classification Search
None
See application file for complete search history.

(56) References Cited

U.S. PATENT DOCUMENTS 5,643,757 A * 7/1997 Malik .................. C07K 14/775
                                                      435/252.33

OTHER PUBLICATIONS

International Search Report dated Dec. 21, 2015 in corresponding Application No. PCT/EP2015/071619; 10 pgs.
Oganesyan et al., "Effect of osmotic stress and heat shock in recombinant protein overexpression and crystallization", Protein Expr Purit., 52(2): 280-285., Available on line Oct. 10, 2006, 6 pgs.
Stephens LL et al., "Co-expression of the Plasmodium falciparum molecular chaperone, PfHsp70, improves the heterologous production of the antimalarial drug target GTP cyclohydrolase I, PfGCHI.", Protein Expr Purif., 77 (2):159-165, Available on line Jan. 22, 2011, 8 pgs.
Guillaume Marcion, et al., "C-terminal amino acids are essential for human heat shock protein 70 dimerization", Cell Stress Chaperones., Jan. 2015; 20(1): 61-72., Published online Jul. 17, 2014, 12 pgs.
Nishihara et al., "Chaperone coexpression plasmids: differential and synergistic roles of DnaK-DnaJ-GrpE and GroEL-GroES in assisting folding of an allergen of Japanese cedar pollen, Cryj2, in *Escherichia coli.*", Appl Environ Microbiol. May 1998;64(5):1694-9., 6 pgs.
Lee SC et al., "Effect of overproduction of heat shock chaperones GroESL and DnaK on human procollagenase production in *Escherichia coli.*", J Biol Chem. Feb. 15, 1992;267(5): 2849-52., 4 pgs.
Studier et al., "Protein production by auto-induction in high density shaking cultures.", Protein Expr Purif. May 2005;41(1):207-34., 28 pgs.

* cited by examiner

*Primary Examiner* — James S Ketter
(74) *Attorney, Agent, or Firm* — Maier & Maier, PLLC

(57) ABSTRACT

A method for the expression of a protein of interest by a bacterium, notable in that it comprises the culturing of a bacterium temporarily or continuously expressing an Hsp protein, in that said bacterium also comprises a nucleic acid sequence, encoding a protein of interest, under the control of a lac promoter and in that said bacterium is cultured in a medium which does not contain IPTG or a metabolized molecule in such a way as to automatically induce the induction of transcription from the lac promoter.

23 Claims, No Drawings

AUTO-INDUCIBLE EXPRESSION SYSTEM

FIELD OF THE INVENTION

The present invention relates in particular to a bacterium suitable for the high-level expression of a protein of interest. The present invention also relates to a method for producing a protein of interest using a bacterium according to the invention. Moreover, the present invention also relates to a set of parts suitable for obtaining a bacterium according to the invention.

PRIOR ART

The production of recombinant proteins, such as enzymes, hormones and antibodies, is necessary in numerous fields such as research in biology, human or veterinary medicine and the food industry. This production is frequently made in prokaryotic cells and more particularly in *Escherichia coli* (*E. coli*).

The lac promoter is the most frequently used inducible promoter for the expression of protein in *E. coli*. It can particularly be used to induce the expression of T7 polymerase. In this system, the gene encoding T7 polymerase is inserted in the bacterial chromosome under the control of the lac operon. The addition of isopropyl-β-D galactoside (IPTG) in the culture medium makes it possible to effectively induce the transcription of T7 polymerase which will subsequently be capable of inducing the transcription of a gene, encoding a heterologous protein, placed under the control of a specific T7 polymerase promoter.

However, IPTG has limitations for the industrial production of recombinant proteins. These limitations are particularly associated with the cost and toxicity of IPTG. Moreover, IPTG must be introduced at a very specific time in the bacterial growth which involves the need for precise monitoring of the cell density in the culture medium.

In order to work around the problems associated with IPTG, various strategies have been used. Of these, mention can particularly be made of the use of lactose or galactose as a transcription inducer. However, the latter are not suitable for attaining equivalent production levels to IPTG and always require precise monitoring of bacterial growth.

Auto-inducible systems using specific culture media, comprising metabolised molecules in such a way as to automatically induce the induction of transcription from the lac promoter, have also been proposed.

The latter systems, though effective, may use molecules or media which are not yet approved by regulatory authorities. Therefore, there is a need for novel bacteria capable of expressing in an auto-inducible fashion a heterologous protein under the control of a lac promoter in a culture medium not comprising toxic molecules.

SUMMARY OF THE INVENTION

As such, the present invention relates in particular to a method for the expression of a protein of interest by a bacterium, notable in that it comprises the culturing of a bacterium temporarily or continuously expressing an Hsp protein, in that said bacterium further comprises a nucleic acid sequence, encoding a protein of interest, under the control of a lac promoter and in that said bacterium is cultured in a medium not containing IPTG.

The present invention also relates to a method for the expression of a protein of interest by a bacterium, notable in that it comprises the culturing of a bacterium temporarily or continuously expressing an Hsp protein, in that said bacterium further comprises a nucleic acid sequence, encoding a protein of interest, under the control of a lac promoter and in that said bacterium is cultured in a medium not containing a metabolised molecule in such a way as to automatically induce the induction of transcription from the lac promoter.

Within the scope of the present invention, the term "a medium not containing a metabolised molecule in such a way as to automatically induce the induction of transcription from the lac promoter" means that said medium does not contain said molecule at the time of introduction of said bacteria and that said molecule is not introduced, externally, into said medium in the course of the method according to the invention.

It was observed, surprisingly, that the expression of an Hsp protein by the bacterium induced, even in the absence of IPTG, the transcription of the nucleic acid sequences under the control of a lac promoter. Although particular IPTG-free culture media or conditions can result in the induction of the transcription of these sequences (see for example Studier et al. protein expression and purification, academic press, vol. 41, 1, 2005, 207-234 or the product Overnight Express™ Autoinduction Systems from Novagen), the specific combination of a lac promoter and an Hsp protein makes it possible to obtain this induction while using conventional culture media and conditions.

Within the scope of the present invention, the term "lac promoter" refers to a promoter of the lac operon, the transcription activity whereof is repressed by a repressor protein such as the LacI protein encoded by the lacl gene but raised by an inducer, such as lactose or analogues thereof (for example, isopropyl-β-D galactoside (IPTG)). The inducer binds with the repressor protein and prevents the repression of gene transcription.

Within the scope of the present invention, the term "under the control" means that the transcription of the nucleic acid sequence, encoding said protein of interest, is dependent on the association of a polymerase on said promoter. Advantageously, said lac promoter is placed upstream from said nucleic acid sequence, encoding said protein of interest.

According to a preferred embodiment of the invention, said protein of interest is not β-galactosidase, lactose permease and/or thiogalactoside transacetylase.

According to a preferred embodiment of the invention, said protein of interest is a heterologous protein.

Within the scope of the present invention, the term "heterologous protein" means that said protein is not a protein naturally expressed by said bacterium.

According to a preferred embodiment, said nucleic acid encoding a protein of interest is comprised in a first plasmid. Within the scope of this embodiment, said plasmid comprises the lac promoter.

According to a preferred embodiment, said protein of interest is a recombinant protein and even more preferably a mammalian protein and particularly preferably a human protein. According to an even more preferred embodiment, said recombinant protein is not a polymerase.

According to a further preferred embodiment, said protein of interest is a polymerase. According to an even more preferred embodiment, said polymerase is a T7 polymerase.

Within the scope of the latter two embodiments, the bacterium according to the invention further comprises a second nucleic acid sequence, encoding a second protein of interest placed under the control of a specific promoter of said polymerase. As such, in this embodiment, the induction of the expression of the polymerase will enable the expression of the protein of interest. According to a preferred embodiment, said second nucleic acid sequence is comprised in said first plasmid or in a second plasmid. According to an even more preferred embodiment, said sequence encoding the polymerase under the control of a Lac promoter is comprised in the genome of said bacterium.

According to a preferred embodiment, said Hsp protein is encoded by a nucleic acid sequence under the control of a lac promoter.

According to a preferred embodiment, said bacterium is an *E. coli*.

According to a preferred embodiment, said bacterium belongs to the BL21(DE3) star strain or to the BL21(DE3) strain.

Within the scope of the present invention, the term "Hsp protein" makes reference to "heat shock proteins", i.e. proteins belonging to the group of proteins the expression whereof is naturally induced by a heat shock. These proteins are well-known to those skilled in the art. They are particularly involved in folding and unfolding other proteins. The expression thereof is increased when the cells are exposed to high temperatures or to other forms of stress. Hsp are found in almost all living organisms, from bacteria to humans. Heat shock proteins are named according to the molecular weight thereof. For example, Hsp60, Hsp70 and Hsp90 refer to families of heat shock proteins of the order of 60, 70 and 90 kilodaltons in size, respectively.

Within the scope of the present invention, the term "Hsp protein" makes reference to Hsp proteins produced naturally by eukaryotic or prokaryotic cells. The term "Hsp protein" also makes reference to proteins exhibiting a sequence having a homology greater than 90%, preferentially greater than 95% and particularly preferentially greater than 99% with naturally produced Hsp proteins. Within the scope of the present invention, is considered to be a protein sequence homologous with another protein sequence, a protein which has, on a number of amino acids at least equal to 80 percent of the number of amino acids of the reference protein sequence, preferably on the total length of the reference sequence, a percentage of homology corresponding to the values stated above. The percentage of homology is calculated by counting the number of positions for which the protein sequences have identical amino acids and by dividing this number of identical positions by the length of the sequence of the longest polypeptide and by multiplying the result obtained by 100 to obtain the percentage of homology between these two sequences.

According to a preferred embodiment, the Hsp protein is chosen in the group comprising Hsp27 (P04792), Hsp40 (P25685), Hsp60 (P10809), Hsp70 (P08107), Hsp90 (P08238 and P07900) and Hsp110 (Q92598) (Uniprot reference number). According to a preferred embodiment, the Hsp protein is human Hsp70 protein (Uniprot reference number): P08107).

According to a preferred embodiment, said bacterium is cultured in a liquid medium.

Surprisingly, the applicant observed that the glucose and/or lactose concentration of the culture medium used makes it possible to modulate the time when the protein of interest is expressed by the bacterium according to the invention.

As such, according to a preferred embodiment of the invention, the culture medium comprises glucose. According to an even more preferred embodiment, said culture medium comprises between 0.01% and 0.5% glucose and according to a particularly preferred embodiment between 0.3% and 0.7% glucose.

As such, according to a further preferred embodiment of the invention, the culture medium comprises lactose.

According to an even more preferred embodiment, said culture medium comprises between 0.01% and 0.5% lactose and according to a particularly preferred embodiment between 0.3% and 0.7% lactose.

DESCRIPTION OF EMBODIMENTS

Expression of Heterologous Proteins by a Bacterium Expressing Human Hsp70
Materials and Methods In all the experiments hereinafter, an *E. coli* BL21(DE3) star bacterial strain was used. However, the invention is not restricted to this particular type of bacteria.

The sequence encoding human Hsp70 was cloned in the bacterial expression plasmid pET21d and placed under the control of the T71ac promoter. This plasmid further contains an ampicillin resistance gene.

The plasmid pET21d-Hsp70 was used to convert *E. coli* BL21(DE3)Star and obtain a bacterium capable of expressing Hsp70.

A second pET plasmid comprising a kanamycin resistance gene and the same origin of replication as the plasmid pET21d was used to clone a gene encoding a heterologous protein. This second plasmid was used to convert the bacterial strain encoding Hsp70.

The production of five different heterologous proteins was tested, these proteins are:
Methionine sulphoxide reductase B (MsrB) from *Xanthomonas compestris*.
Thioredoxin 1 (Trx1) from *E. coli*.
Purine nucleoside phosphorylase (PNP) from *E. coli*.
The N-terminal domain of the T1R3 receptor from *Homo sapiens*.
Miraculin from *Richardella dulcifica* (MCL).

These five proteins are from different sources (bacterium, plant or human) and of sizes varying from 14 kDa to 45 kDa. Moreover, they exhibit different functions (enzyme, receptor or ligand) and cellular locations (cytoplasm, plasma or membrane).

The converted bacteria were cultured in LB medium, in different volumes (5 ml, 20 ml, 1 l) at different temperatures (25° C., 30° C. and 37° C.)

The culture media obtained were analysed by PAGE-SDS electrophoresis.
Results

All the proteins tested are expressed at a high level at 37° C. in the absence of inducer. As such, it can be observed on the PAGE-SDS electrophoreses that the heterologous protein is the protein most strongly expressed by the bacterium.

An accumulation of heterologous proteins is observed for at least 20 hours.

The production of heterologous proteins is not dependent on the volume of culture medium used.

These results are obtained at all temperatures compatible with bacterial growth.

The method according to the invention was implemented, with the same success, with heterologous proteins from mammals (particularly humans), bacteria and plants. Of these, mention can particularly be made of GSTs from humans (GSTA1 and GSTP1), drosophila (GSTD2 and GSTD7), a human lipocalin (LCN1), and human Hsp110.

The method according to the invention also functions regardless of the location of the protein: membranous, extracellular or cytoplasmic.

The method according to the invention is not dependent on the structure of the plasmid used and was successfully implemented with the plasmids pD431-SR, pD451-SR, pD434-SR, pD434-WR, pD454-WR, pJ431:2047, pJ414:2047 (DNA2.0 Menlo Park, USA).

Effects of Glucose and Lactose on the Expression of the Proteins of Interest

Materials and Methods

The converted bacteria for expressing the recombinant proteins cited above were cultured in LB medium supplemented with 0.05% glucose or 0.2% lactose.

The bacterial growth was monitored by measuring the optical density at 600 nm and the quantity of recombinant protein produced was measured by PAGE-SDS chromatography of the culture supernatant.

Results

In the absence of glucose or lactose, the expression of the proteins of interest appears at an optical density of 1.

Adding 0.05% glucose in the medium delays the expression of the protein of interest to an optical density at 600 nm of 1.5.

Adding 0.02% lactose makes it possible to accelerate the production of the protein of interest to an optical density of 0.7.

The invention claimed is:

1. A method for an expression of a protein of interest by a bacterium comprising:
   culturing of the bacterium temporarily or continuously expressing an Hsp protein encoded by a first nucleic acid sequence under a control of a lac promoter,
   wherein said bacterium further comprises a second nucleic acid sequence encoding a protein of interest under the control of the lac promoter, and
   wherein said bacterium is cultured in a medium not containing IPTG or a metabolised molecule in such a way as to automatically induce an induction of transcription from the lac promoter.

2. The method according to claim 1, wherein said second nucleic acid encoding the protein of interest is comprised in a first plasmid.

3. The method according claim 1, wherein said protein of interest is a recombinant protein.

4. The method according to claim 1, wherein said protein of interest is a polymerase.

5. The method according to claim 4, wherein said polymerase is a T7 polymerase.

6. The method according to claim 4, wherein said bacterium further comprises a third nucleic acid sequence encoding a second protein of interest placed under the control of a specific promoter of said polymerase.

7. The method according to claim 6, wherein said third nucleic acid sequence is comprised in a first plasmid or in a second plasmid.

8. The method according to claim 1, wherein said bacterium is an *E. coli*.

9. The method according to claim 8, wherein said bacterium belongs to a BL21(DE3) strain or to a BL21(DE3) star strain.

10. The method according to claim 1, wherein the Hsp protein is chosen in the group comprising Hsp40, Hsp70, Hsp90 and Hsp110.

11. The method according to claim 1, wherein the Hsp protein is human Hsp70 protein.

12. The method according to claim 1, wherein said bacterium is cultured in a liquid medium.

13. A method for an expression of a protein of interest by a bacterium comprising:
    culturing of the bacterium temporarily or continuously expressing a human Hsp70 protein encoded by a first nucleic acid sequence,
    wherein said bacterium further comprises a second nucleic acid sequence encoding a protein of interest under a control of a lac promoter, and
    wherein said bacterium is cultured in a medium not containing IPTG or a metabolised molecule in such a way as to automatically induce an induction of transcription from the lac promoter.

14. The method according to claim 13, wherein said second nucleic acid encoding the protein of interest is comprised in a first plasmid.

15. The method according to claim 13, wherein said protein of interest is a recombinant protein.

16. The method according to claim 13, wherein said protein of interest is a polymerase.

17. The method according to claim 16, wherein said polymerase is a T7 polymerase.

18. The method according to claim 16, wherein said bacterium further comprises a third nucleic acid sequence encoding a second protein of interest placed under the control of a specific promoter of said polymerase.

19. The method according to claim 18, wherein said third nucleic acid sequence is comprised in a first plasmid or in a second plasmid.

20. The method according to claim 13, wherein said human Hsp70 protein is encoded by the first nucleic acid sequence under the control of the lac promoter.

21. The method according to claim 13, wherein said bacterium is an *E. coli*.

22. The method according to claim 21, wherein said bacterium belongs to a BL21(DE3) strain or to a BL21(DE3) star strain.

23. The method according to claim 13, wherein said bacterium is cultured in a liquid medium.

* * * * *